(12) United States Patent
Lafontaine

(10) Patent No.: US 8,585,689 B2
(45) Date of Patent: Nov. 19, 2013

(54) CRYOTREATMENT DEVICES AND METHODS OF FORMING CONDUCTION BLOCKS

(75) Inventor: Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/252,817

(22) Filed: Oct. 4, 2011

(65) Prior Publication Data

US 2012/0022513 A1    Jan. 26, 2012

Related U.S. Application Data

(60) Continuation of application No. 12/485,697, filed on Jun. 16, 2009, now Pat. No. 8,048,066, which is a division of application No. 10/411,601, filed on Apr. 10, 2003, now abandoned.

(51) Int. Cl.
*A61B 18/02* (2006.01)

(52) U.S. Cl.
USPC .............................................. 606/21; 606/23

(58) Field of Classification Search
USPC ....................................................... 606/21, 23
See application file for complete search history.

(56) References Cited

U.S. PATENT DOCUMENTS

| | | | |
|---|---|---|---|
| 3,298,371 A | 1/1967 | Lee | |
| 3,782,386 A | 1/1974 | Barger et al. | |
| 3,913,581 A | 10/1975 | Ritson-Upavon et al. | |
| 4,015,606 A | 4/1977 | Mitchiner | |
| 4,207,897 A | 6/1980 | Lloyd et al. | |
| 4,924,679 A | 5/1990 | Brigham | |
| 5,078,713 A | 1/1992 | Varney | |
| 5,147,355 A | 9/1992 | Friedman et al. | |
| 5,254,116 A | 10/1993 | Baust et al. | |
| 5,281,213 A | 1/1994 | Milder et al. | |
| 5,281,215 A | 1/1994 | Milder | |
| 5,334,181 A | 8/1994 | Rubinsky et al. | |
| 5,403,309 A | 4/1995 | Coleman et al. | |
| 5,403,311 A | 4/1995 | Abele et al. | |
| 5,423,807 A | 6/1995 | Milder | |
| 5,425,582 A | 6/1995 | Asano et al. | |
| 5,501,681 A | 3/1996 | Neuwirth | |

(Continued)

FOREIGN PATENT DOCUMENTS

WO    0137919    5/2001

OTHER PUBLICATIONS

JP Official Action in JP App. Ser. No. 2006-509805, mailed Nov. 10, 2009, 7 pages.

*Primary Examiner* — Lee S Cohen
(74) *Attorney, Agent, or Firm* — Seager Tufte & Wickhem, LLC

(57) ABSTRACT

Cryotreatment devices and methods of ablating tissue within the body are disclosed. A cryotreatment device in accordance with an exemplary embodiment of the present invention includes an elongated member having one or more needle-like ablation tips configured to induce necrosis at a target site within the heart. A cooling fluid such as a cryogen may be injected through a lumen extending into the distal portion of the device. The ablation tips can be configured to pierce and ablate surrounding tissue, blocking electrical stimuli that can cause fibrillations or other arrhythmias of the heart. The device may also include means for controlling the transmural depth at which the ablation tips are inserted into the cardiac tissue. Methods of forming a contiguous line of conduction block in accordance with the present invention are also disclosed.

13 Claims, 4 Drawing Sheets

(56) References Cited

U.S. PATENT DOCUMENTS

| | | |
|---|---|---|
| 5,624,392 A | 4/1997 | Saab |
| 5,674,218 A | 10/1997 | Rubinsky et al. |
| 5,688,267 A | 11/1997 | Panescu et al. |
| 5,716,353 A | 2/1998 | Matsuura |
| 5,733,280 A | 3/1998 | Avitall |
| 5,741,248 A | 4/1998 | Stern et al. |
| 5,743,903 A | 4/1998 | Stern |
| 5,759,182 A | 6/1998 | Varney |
| 5,807,391 A | 9/1998 | Wijkamp |
| 5,853,368 A | 12/1998 | Solomon et al. |
| 5,868,735 A | 2/1999 | Lafontaine |
| 5,885,276 A | 3/1999 | Ammar et al. |
| 5,893,848 A | 4/1999 | Negus et al. |
| 5,899,898 A | 5/1999 | Arless et al. |
| 5,951,546 A | 9/1999 | Lorentzen |
| 5,993,444 A | 11/1999 | Ammar et al. |
| 6,056,743 A | 5/2000 | Ellis et al. |
| 6,063,082 A | 5/2000 | DeVore et al. |
| 6,074,412 A | 6/2000 | Mikus et al. |
| 6,106,518 A | 8/2000 | Wittenberger et al. |
| 6,142,991 A | 11/2000 | Schatzberger |
| 6,161,543 A | 12/2000 | Cox et al. |
| 6,164,283 A | 12/2000 | Lesh |
| 6,237,355 B1 | 5/2001 | Li |
| 6,283,959 B1 | 9/2001 | Lalonde et al. |
| 6,290,696 B1 | 9/2001 | Lafontaine |
| 6,355,029 B1 | 3/2002 | Joye et al. |
| 6,451,012 B2 | 9/2002 | Dobak, III |
| 6,468,268 B1 | 10/2002 | Abboud et al. |
| 6,502,576 B1 | 1/2003 | Lesh |
| 6,506,189 B1 | 1/2003 | Rittman, III et al. |
| 6,527,767 B2 | 3/2003 | Wang |
| 7,147,633 B2 | 12/2006 | Chee et al. |
| 7,479,139 B2 | 1/2009 | Cytron et al. |
| 2002/0040220 A1 | 4/2002 | Zvuloni et al. |
| 2003/0029462 A1 | 2/2003 | Cox et al. |

CRYOTREATMENT DEVICES AND METHODS OF FORMING CONDUCTION BLOCKS

CROSS-REFERENCE TO RELATED APPLICATIONS

This application is a continuation of U.S. application Ser. No. 12/485,697, filed Jun. 16, 2009, now U.S. Pat. No. 8,048,066; which is a divisional of and claims priority to U.S. application Ser. No. 10/411,601, filed Apr. 10, 2003, now abandoned, the entire disclosures of which are all incorporated herein by reference.

FIELD OF THE INVENTION

The present invention relates generally to medical devices for ablating tissue at one or more target sites. More specifically, the present invention relates to cryotreatment devices and methods for inducing controlled necrosis of cardiac tissue within the heart.

BACKGROUND OF THE INVENTION

Cardiac arrhythmias such as atrial fibrillation, bradycardia, ventricular tachycardia, ventricle fibrillation, and Wolff-Parkinson-White syndrome are common heart abnormalities that cause stroke, myocardial infarction, and other thromboembolic events within the body. In patients with normal sinus rhythm, the heart is electrically excited to beat in a synchronous and patterned manner, typically at a rate of 60 to 100 beats per minute (bpm). In contrast, in patients with cardiac arrhythmia, abnormal regions of the cardiac tissue may aberrantly conduct to adjacent tissue, causing the heart to beat irregularly. In ventricular tachycardia, for example, electrical signals may be errantly received in the lower heart chamber (i.e. the ventricle) instead of the right, upper chamber (i.e. the atria), causing the heart to beat rapidly. In atrial fibrillation, the most common type of cardiac arrhythmia, the upper chambers of the heart beat at an uncontrolled rate of 350 to 600 bpm, which results in a reduction of the pumping force of the heart. As a result of this reduced pumping force, blood in the heart chambers may become stagnant and pool, forming blood clots that can dislodge within the body and cause stroke or other life threatening events.

To treat cardiac arrhythmia, a number of therapeutic procedures have been developed, including RF catheter ablation, chemical cardioversion, percutaneous myocardial revascularization (PMR), and suppression. Antiarrhythmic medications such as beta-blockers, calcium channel blockers, anticoagulants, and DIGOXIN have also been used successfully to treat some forms of cardiac arrhythmia. More recent trends have focused on the use of cryotreatment catheters to treat arrhythmias such as atrial fibrillation and ventricular tachycardia. Such devices provide a relatively non-invasive method of treatment in comparison to other surgical techniques.

In one such method, for example, a catheter loaded with a cryogenic cooling fluid may used to cryogenically cool cardiac tissue at strategic locations of the heart, such as the right and left atria, or the pulmonary veins. The catheter can be used to induce necrosis at one or more pre-mapped target sites within the heart to create conduction blocks within the aberrant electrical conduction pathways. In atrial fibrillation, for example, necrosis of one or more target sites within the atrial cardiac muscle tissue can be used to block the electrical signals believed to cause and/or sustain the fibrillation.

In some techniques, the use of a cryotreatment device to form the required conduction block may be ineffective since there is no adequate means to control the transmural depth of the lesion, or the distance between each lesion. To compensate for these shortcomings, many cryotreatment devices utilize relatively large catheter tips, which destroy more tissue than is necessary to form the conduction block and further reduce the already weakened pumping force of the heart. It is therefore desirable to have a cryotreatment device capable of transmurally controlling the depth of each lesion and in a contiguous manner.

SUMMARY OF THE INVENTION

The present invention relates generally to cryotreatment devices and methods for reducing or eliminating arrhythmia by inducing controlled necrosis at one or more pre-mapped target sites within the heart. A cryotreatment device in accordance with an exemplary embodiment of the present invention may comprise an elongated member having a proximal portion, a distal portion, and one or more lumens therein in fluid communication with a cooling fluid adapted to cool the distal portion of the elongated member. The elongated member may include one or more needle-like ablation tips configured to pierce and necrotize cardiac tissue within the heart, preventing the conduction of aberrant electrical signals through the tissue to one or more relay sites of arrthymogenic foci. The cryotreatment device may include one or more features configured to form an array of ablations within the cardiac tissue, forming a contiguous line of conduction block.

The ablation tips may be retractable within the elongated member to control the penetration depth of the tips transmurally into the cardiac tissue. A pull cord operatively coupled to the ablation tip can be used to retract the ablation tip from the cardiac tissue. An ultrasonic probe or other measuring device may also be provided to measure and control the insertion depth of the cryotreatment device within the cardiac tissue.

A cryosurgical method in accordance with the present invention may comprise the steps of providing a cryotreatment device to a target site within the heart, and necrotizing one or more locations within the cardiac tissue to form a contiguous line of conduction block. A cooling fluid such as liquid nitrous oxide can be injected through an inner lumen extending to the distal portion of the cryotreatment device to cool the surrounding tissue adjacent the ablation tips.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
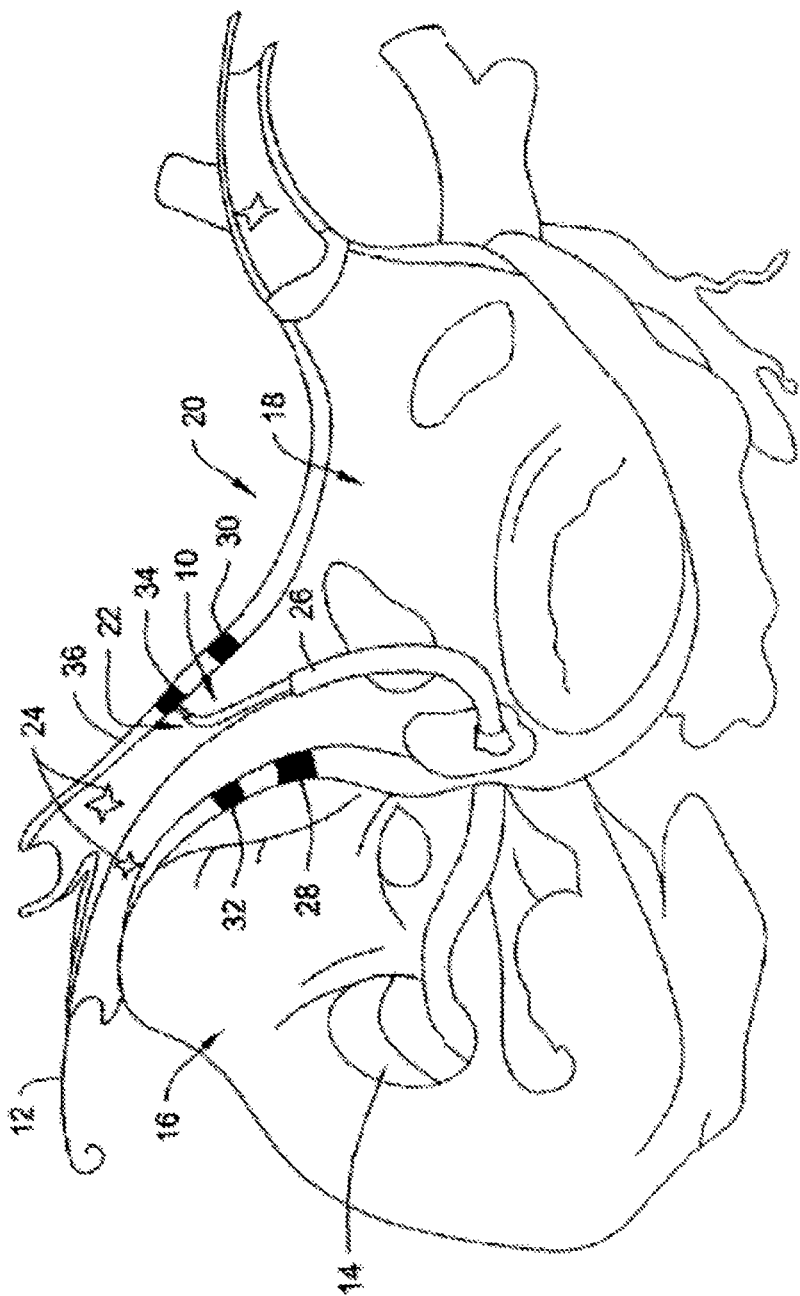
FIG. 1 is an illustration of a cryotreatment device in accordance with an exemplary embodiment of the present invention, wherein the device is shown inserted through the septal wall of the heart and advanced to a target site at or near one or more relay points.

FIG. 1 is an illustrative view of a cryotreatment device 10 in accordance with an exemplary embodiment of the present invention for inducing controlled necrosis at one or more pre-mapped target sites within the heart. A guide wire 12 inserted percutaneously into the femoral or jugular veins is shown advanced through the septal wall 14 and into the upper chambers 16,18 of a heart 20. Using known manipulation techniques in the art, guidewire 12 can be advanced to a location distal a target site 22 determined to cause electrical interference with one or more downstream arrythmogenic foci 24. A guide catheter 26 sufficiently sized to receive cryotreatment device 10 can be used to advance the cryotreatment device 10 to a location at or near the target site 22.

Arrhythmias such as atrial flutter, atrial fibrillation and ventricular tachycardia are typically caused when abnormal regions of the heart transmit aberrant electrical signals vis-a-vis arrythmogenic foci. To treat such arrhythmias, a cryotreatment device in accordance with the present invention can be inserted into cardiac tissue at a pre-mapped target site and cooled to a temperature of about −40 to −100° C. to induce necrosis at one or more locations 28,30,32,34 within the heart, such as the pulmonary vein 36. The cryotreatment device can be inserted at the various locations 28,30,32,34 to form a line of conduction block that prevents certain electrical signals from being sent from the foci points 24. In necrotizing the cardiac tissue at several locations, thereby forming a line of conduction block in the pulmonary vein 36, the transmission of aberrant signals believed to cause the arrhythmia can be reduced or in some cases altogether eliminated.

Figure 2:
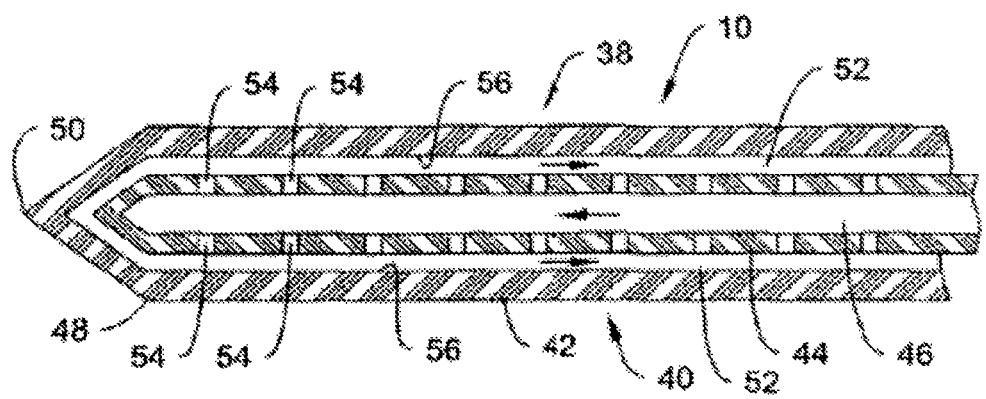
FIG. 2 is a partial cross-sectional view of the cryotreatment device of FIG. 1.

FIG. 2 is a partial cross-sectional view of the cryotreatment device 10 of FIG. 1, showing the distal portion 38 of the device 10 in greater detail. In the exemplary embodiment of FIGS. 1-2, cryotreatment device 10 comprises a multiple lumen catheter body 40 having an outer shaft 42 configured to pierce and cool the cardiac tissue, and an inner shaft 44 defining an inner lumen 46 in fluid communication with a cooling fluid. The outer shaft 42 of catheter body 40 may have a transverse cross-sectional area that is substantially circular in shape, extending from a proximal end (not shown) located outside of the patient's body to a transition region 48 on the catheter body 40. At transition region 48, catheter body 40 tapers distally to a needle-like ablation tip 50 configured to pierce and contact cardiac tissue.

To cool the distal portion 38 of cryotreatment device 10 to a sufficiently low temperature to induce necrosis when inserted into cardiac tissue, cryotreatment device 10 can be placed in fluid communication with a cooling fluid such as liquid nitrogen, nitrous oxide ($N_2O$), carbon dioxide ($C_2O$), chlorodifluoromethane, polydimethysiloxane, ethyl alcohol, chlorofluorocarbons (Freon), or other suitable fluid. The cooling fluid can be delivered in either a liquid or gas state through inner lumen 46, and injected into the annular space 52 between the outer and inner shafts 42,44 through several apertures 54 disposed in the inner shaft 44. In one embodiment, for example, pressurized liquid nitrous oxide can be fluidly coupled to the inner lumen 46 of catheter body 40, and ejected through several apertures 54 disposed in the inner lumen 44. Using the Joule-Thompson cooling effect, the apertures 54 are adapted to act as a throttling element (e.g. a throttling nozzle) for the cryogen, producing isenthalpic cooling as the fluid is expended from a relatively high pressure within the inner lumen 46 to a lower pressure as it enters the annular space 52. As the cryogenic fluid expands as it passes through the apertures 54, it transitions to a gas and impinges upon the interior wall 56 of the outer shaft 42 cooling the distal portion 38 of the catheter body 40. This temperature drop is then thermally transferred through the catheter body 40 and into the surrounding cardiac tissue 58, inducing necrosis at the target site 22. The cryogenic fluid is subsequently returned through annular lumen 52 to the proximal end of the device 10.

The number of apertures 54 can be varied to provide a desired temperature decrease to the distal portion 38 of the catheter body 40. The type of cryogen used and the pressure and/or volume at which the cryogen is delivered through the inner lumen 46 can also be selected to impart a particular cooling characteristic to the device 10, as desired. In the exemplary embodiment of FIGS. 1-2, cryotreatment device 10 includes several equidistantly spaced apertures 54 configured to provide uniform cooling through the distal portion 38 of the catheter body 40. It should be recognized, however, that the apertures 54 could be placed at any number of strategic locations, at either equidistant or non-equidistant intervals, to direct the cryogenic fluid to a particular location within the device 10.

The outer and inner shafts 42, 44 of cryotreatment device 10 may be fabricated from materials having certain desirable flexibility and thermodynamic properties. For example, the outer and inner shafts 42, 44 may each be formed of a super-elastic material such as nickel-titanium alloy (Nitinol) to permit the cryotreatment device 10 to be inserted through relatively tortuous locations of the body without kinking. Other suitable biocompatible materials such stainless steel or a polymer/metal composition may also be utilized, depending on the particular application.

Figure 3:
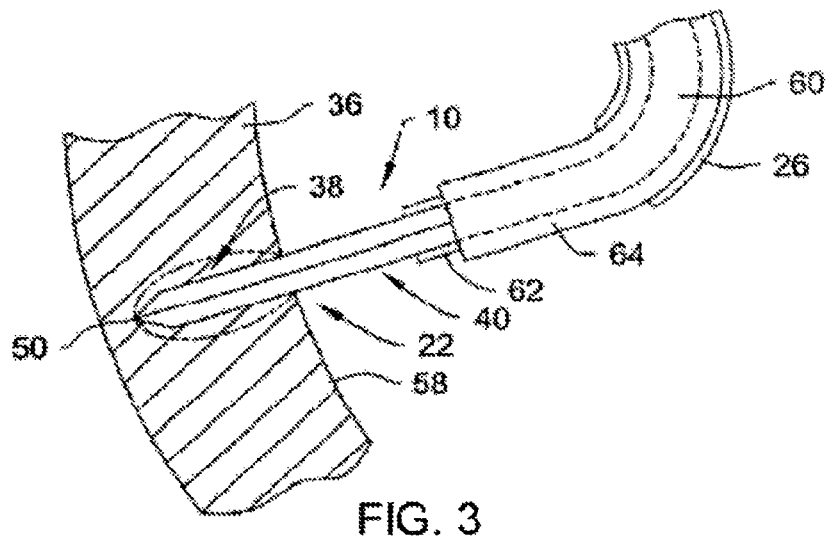
FIG. 3 is a detailed view of the cryotreatment device of FIGS. 1-2, wherein the device includes an ultrasonic probe adapted measure and control the transmural depth of the device into the cardiac tissue.

Referring now to FIG. 3, methods of using cryotreatment device 10 will now be described in the context of a cryosurgical procedure to necrotize cardiac tissue 58 within a body lumen such as a pulmonary vein 36. Cryotreatment device 10 can be inserted through a previously positioned guide catheter 26 and advanced to a pre-mapped target site 22 within the heart believed to transmit aberrant electrical signals to one or more relay points. As shown in FIG. 3, needle-like ablation tip 50 of device 10 can be configured to pierce and contact the cardiac tissue 58 of pulmonary vein 36, allowing the distal portion 38 of catheter body 40 to be inserted into the cardiac tissue 58. A curved portion 60 on the catheter body 40 may be adapted to orient the needle-like ablation tip 50 in a direction substantially perpendicular to the tissue wall 58.

In one aspect of the present invention, cryotreatment device 10 can be configured to measure and control the transmural depth at which the device is inserted into the cardiac tissue 58. Controlled insertion of the needle-tip ablation tip 50 into the cardiac tissue 58 prevents distension of the vein 36 from occurring, and prevents the ablation of cardiac tissue not necessary to form the conduction block. Controlled insertion of the needle-like ablation tip 50 into the cardiac tissue 58 also ensures that the cryotreatment device 10 is inserted at a sufficient depth to form the desired conduction block.

An ultrasonic probe 62 or other measurement device may be utilized to measure the precise depth at which cryotreatment device 10 is inserted into the cardiac tissue 58. The ultrasonic probe 62 can be coupled to catheter body 40 a predetermined distance from the needle-like ablation tip 50, and engaged to acoustically measure the depth at which the distal portion 38 is inserted into the cardiac tissue 58. The ultrasonic probe 62 may be coupled to the catheter body 40, or may be formed as a separate element that can be advanced along the catheter body 40 and positioned proximal the cardiac tissue 58. In one exemplary embodiment, the ultrasonic probe 62 may act as a guiding member for the device 10, eliminating the need for a separate guide catheter. Those of skill in the art will readily recognize that other suitable devices for measuring the insertion depth of the cryotreatment device 10 may be employed, including, for example, the use of an optical probe, acoustic reflective coatings, distal bipolar electrodes, or through the use radiographic techniques such as fluoroscopic marker bands.

In operation, a fluid controller or other similar device can be coupled to the proximal end of the cryotreatment device 10 and used to inject a controlled flow of cryogenic fluid (e.g. liquid $N_2O$) through the inner lumen 46. One or more temperature sensors 39 on the distal portion 38 of catheter body 40 may also optionally be used to monitor the temperature of the device 10 and adjust the flow rate via the fluid controller, as necessary. An insulated sleeve 64 surrounding the catheter body 40 may be utilized to thermally isolate the catheter body 40 proximal the distal portion 38 to prevent ablating other areas of the body.

Figure 4:
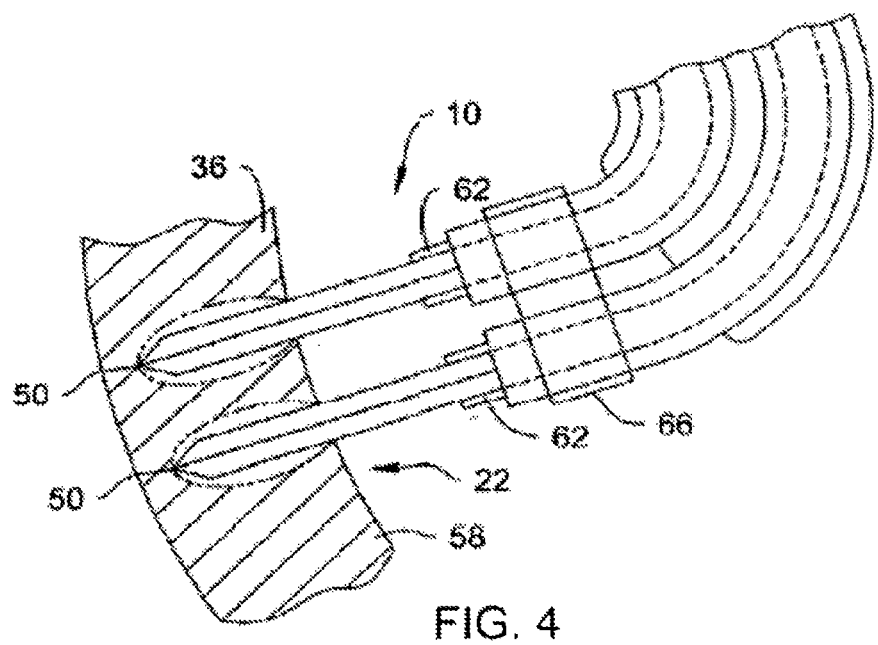
FIG. 4 is another detailed view illustrating multiple cryotreatment devices coupled together using a coupling member.

In certain embodiments, the cryotreatment device may include a coupling member configured to couple multiple ablation tips together in an array. As shown in FIG. 4, for example, a coupling member 66 can be used to connect multiple cryotreatment devices 10 together, forming a linear array of needle-like ablation tips 50 that, when thermally cooled via a cryogenic fluid, create a line of contiguous conduction block along the cardiac tissue 58 at the target site 22. The coupling member 66 can be configured to couple together any number of cryotreatment devices together in any desired array or pattern. The multiple cooling members 10 applied in a sequential cooling method will allow the lesions to be made in a stitched like fashion to ensure contiguous connection of all the lesions. The method of stitching is accomplished by moving one needle 50 while the other needle 50' is anchored and froze into the tissue. The sequence of operation would be as follows:
1. Insert two needles at start point and apply maximum freeze;
2. Thaw the proximal needle and reduce temperature on distal needle;
3. Retract proximal needle and rotate around anchored distal needle;
4. Apply maximum cooling on both needles and repeat steps 2-4.

Figure 5:
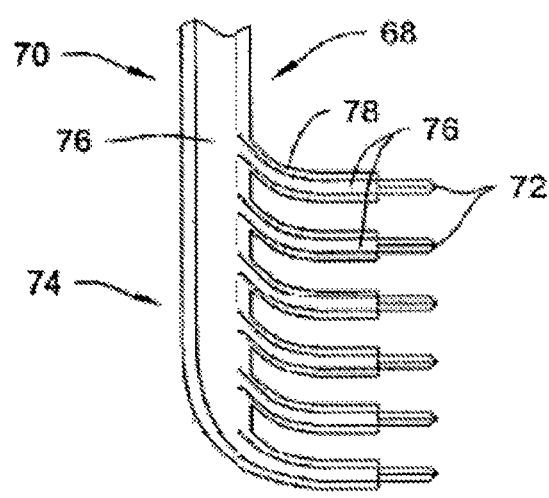
FIG. 5 is a view of a cryotreatment device in accordance with an exemplary embodiment of the present invention, wherein the cryotreatment device includes a linear array of ablation tips.

FIG. 5 is a view of a cryotreatment device 68 in accordance with another exemplary 20 embodiment of the present invention. Cryotreatment 68 comprises a catheter body 70 having several linearly disposed ablation tips 72 along a distal portion 74 that, when placed into fluid communication with a cryogenic cooling fluid, are configured to form a line of conduction block within a target site of the heart. Each ablation tip 72 may be configured similar to tip 50 described above, having a needle-like shape configured to pierce and contact the cardiac tissue when inserted. The number of needles 72 and lumens 76 may be the same as shown, or may be as few as two needles 72 for any number of lumens 76 in the method previously described. An inner lumen 76 in fluid communication with a source of pressurized cryogen at or near the proximal end of the device 70 is configured to cool each ablation tip 72 in a manner similar that described above with respect to cryotreatment device 10. The cryotreatment device 70 may also optionally include an ultrasonic probe or other measurement means (not shown) for measuring the precise depth at which the ablations tips 72 are transmurally inserted into the cardiac tissue. An insulation layer 78 surrounding the catheter body 70 thermally insulates the body 70 from ablating other areas of the body.

To form a line of conduction block within a target site of the heart, ablation tips 72 can be aligned with a portion of the cardiac tissue believed to transfer the aberrant electrical signal(s) to one or more downstream relay points, and inserted into the tissue at a controlled depth. A pressurized cryogenic fluid can be delivered through the catheter body 70, causing the ablation tips 72 on the distal portion 74 to undergo a temperature drop to a temperature of about −40 to −100° C., inducing necrosis in the surrounding cardiac tissue.

The destruction of more tissue than is necessary to form the conduction block may be mitigated through the use of a series of smaller ablation tips. Moreover, the number, shape and arrangement of the ablation tips may be varied in accordance with the particular application. In certain applications, for example, a cryotreatment device in accordance with the present invention may be configured to form a circumferential line of conduction blocks at a target site within the heart.

Figure 6:
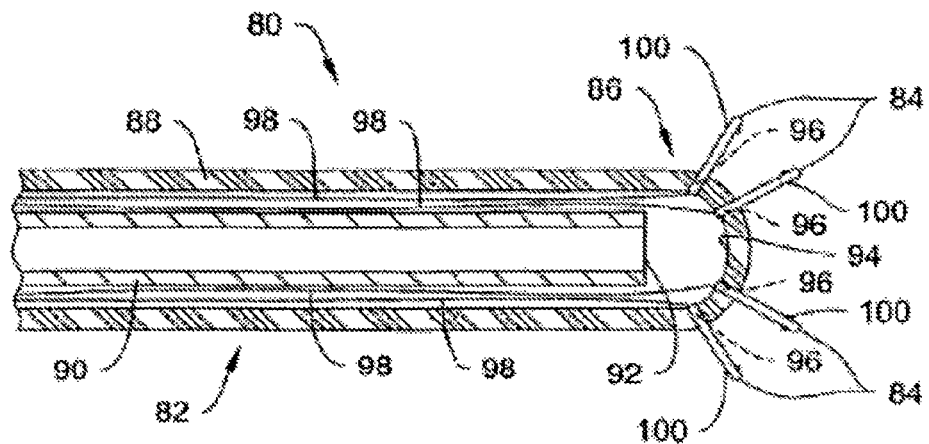
FIG. 6 is a partial cross-sectional view of a cryotreatment device in accordance with an exemplary embodiment of the present invention, wherein the cryotreatment device includes several retractable cryogenic tips configured to form a circumferential line of conduction block within the heart.

In one exemplary embodiment shown in FIG. 6, a cryotreatment device 80 in accordance with the present invention may include a catheter body 82 having several needle-like ablation tips 84 on distal end 86 that, when thermally cooled via a supplied source of cryogenic fluid, form a circumferential line of conduction block at a target site within the heart (e.g. about a pulmonary vein). Cryotreatment device 80 may comprise an outer shaft 88, and an inner shaft 90 disposed within the outer shaft 88. The inner shaft 90 can be configured to deliver a pressurized source of cryogenic fluid such as liquid nitrogen or $N_2O$ through aperture 92 towards the interior surface 94 of distal end 86, causing the interior surface 94 of the distal end 86 of catheter body 82 to cool and conduct heat.

Each of the needle-like ablation tips 84 can be configured to retract through several openings 96 disposed on the distal end 86 of the catheter body 82. A control wire 98 extending proximally from each ablation tip 84 to a location outside of the patient's body may be used to retract each tip 84 through its respective opening 96, allowing the operator to adjust the precise depth at which the tip 84 is inserted the cardiac tissue. A flange 100 coupled to each ablation tip 84 prevents the tip 84 from being pulled proximally through opening 96 as control wire 98 is retracted. As with any of the other embodiments described herein, an ultrasonic probe or other suitable device can be utilized to measure and, if necessary, control the penetration depth of the ablation tips 84 within the tissue.

In use, cryotreatment device 80 can be advanced to a target site within the heart, and, with the ablation tips 84 initially in a fully deployed position, inserted into the cardiac tissue. Once the device 80 is inserted into the tissue, the operator can retract the control wire 98 proximally a distance, causing the ablation tips 84 to retract from within the tissue a slight distance (e.g. 0.5-3.0 cm). An ultrasonic probe or other suitable device may be used to measure the precise depth at which the ablation tips 84 are inserted into the cardiac tissue. At the desired depth, a pressurized flow of cryogen is then delivered through the device, causing the distal end 86 of the device, including the ablation tips 84, to cool to a temperature of about −40 to −100° C., forming a circumferential line of conduction block within the body.

Figure 7:
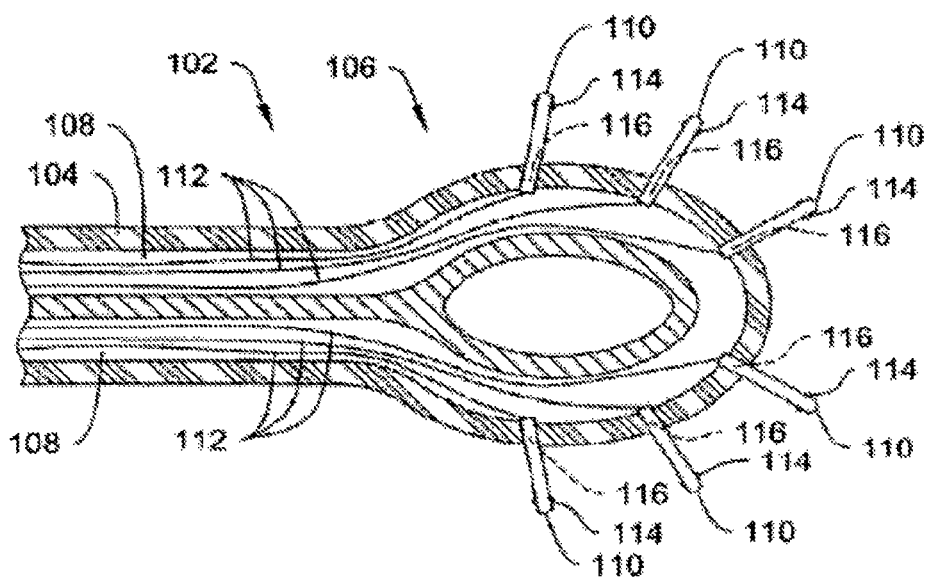
FIG. 7 is a partial cross-sectional view of a cryotreatment device in accordance with another exemplary embodiment of the present invention, wherein the cryotreatment devices includes an enlarged distal portion with retractable ablation tips.

FIG. 7 is a partial cross-sectional view of a cryotreatment device 102 in accordance with another exemplary embodiment of the present invention. Cryotreatment device 102 comprises an outer shaft 104 having a proximal portion (not shown), a distal portion 106, and an inner lumen 108 in fluid communication with a cooling fluid such as liquid $N_2O$. The distal portion 106 of cryotreatment device 102 may be enlarged slightly, orienting several retractable needle-like ablation tips 110 in a wider radial array, permitting the formation of a circumferential line of conduction block at larger target sites. A control wire 112 operatively coupled to each ablation tip 110 can be utilized to adjust the transmural depth of the tip 110 into the cardiac tissue. A flanged portion 114 on each ablation tip 110 prevents the operator from pulling the ablation tip 110 proximally through the tip openings 116 on the distal portion 106 of the outer shaft 104.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A medical device for inducing controlled necrosis at a target site within the body, comprising:
    an elongated member having a proximal portion, a distal portion, and a lumen therein providing a cooling fluid path, wherein the lumen is a lumen of an inner shaft disposed in an outer shaft, and the inner shaft includes at least one aperture configured to eject cooling fluid from said inner shaft onto an interior surface of the elongated member;
    a plurality of ablation tips in communication with said cooling fluid path near the distal portion of said elongated member configured to contact and ablate tissue; and
    a plurality of control wires operatively connected to the plurality of ablation tips to control the transmural depth of said plurality of ablation tips in to the tissue.

2. The medical device of claim 1, wherein the elongated member comprises a plurality of openings in the distal portion through which the plurality of ablation tips extend.

3. The medical device of claim 2, wherein each of the plurality of ablation tips comprises a flange.

4. The medical device of claim 1, further comprising an ultrasonic sensor mounted so as to move toward the tissue as the ablation tip moves into the tissue.

5. The medical device of claim 3, wherein the plurality of flanges are proximal the plurality of openings.

6. The medical device of claim 1 wherein the plurality of ablation tips is retractable within the distal portion of the elongated member.

7. The medical device of claim 1 wherein the plurality of ablation tips is linearly arranged along an arcuate line on the distal portion of said elongated member.

8. The medical device of claim 1 wherein the plurality of ablation tips is configured to form a line of conduction block at said target site.

9. The medical device of claim 1 further comprising a guiding member configured to transport said elongated member to the target site.

10. A medical device for inducing controlled necrosis at a target site within the body, comprising:
    an elongated member having a proximal portion, a distal portion, and a lumen therein providing a cooling fluid path, wherein the lumen is a lumen of an inner shaft disposed in an outer shaft, and the inner shaft includes a distal aperture configured to eject cooling fluid from said inner shaft onto an interior surface of the elongated member;
    a plurality of ablation tips in communication with said cooling fluid path near the distal portion of said elongated member configured to form a line of conduction block; and
    a plurality of control wires operatively connected to the plurality of ablation tips to control the transmural depth of said plurality of ablation tips in to the tissue.

11. The medical device of claim 10 wherein the plurality of ablation tips is linearly arranged along the distal portion of said elongated member.

12. The medical device of claim 10 further comprising a guiding member configured to transport said elongated member to the target site.

13. The medical device of claim 10 wherein the plurality of ablation tips are needle-like ablation tips.

* * * * *

UNITED STATES PATENT AND TRADEMARK OFFICE
CERTIFICATE OF CORRECTION

PATENT NO.        : 8,585,689 B2           Page 1 of 1
APPLICATION NO.   : 13/252817
DATED             : November 19, 2013
INVENTOR(S)       : Daniel M. Lafontaine It is certified that error appears in the above-identified patent and that said Letters Patent is hereby corrected as shown below:

In the Specification

Column 3
Line 42: after "- 100°C", delete "."

Column 6
Line 26: after "- 100°C", delete "."

Column 7
Line 8: after "- 100°C", delete "."

Signed and Sealed this
Third Day of June, 2014

Michelle K. Lee
*Deputy Director of the United States Patent and Trademark Office*